United States Patent
Inoue et al.

(10) Patent No.: US 10,307,212 B2
(45) Date of Patent: Jun. 4, 2019

(54) MEDICAL MANIPULATOR AND CONTROL METHOD OF MEDICAL MANIPULATOR

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 140 days.

(21) Appl. No.: 14/721,447

(22) Filed: May 26, 2015

(65) Prior Publication Data

US 2015/0327940 A1 Nov. 19, 2015

Related U.S. Application Data

(63) Continuation of application No. PCT/JP2014/052370, filed on Jan. 28, 2014.

(Continued)

(51) Int. Cl.
*A61B 1/00* (2006.01)
*A61B 1/31* (2006.01)
(Continued)

(52) U.S. Cl.
CPC ............ *A61B 34/30* (2016.02); *A61B 1/0008* (2013.01); *A61B 1/0016* (2013.01);
(Continued)

(58) Field of Classification Search
CPC .............. A61B 1/00039; A61B 1/0008; A61B 1/00087; A61B 1/00131; A61B 1/00133;
(Continued)

(56) References Cited

U.S. PATENT DOCUMENTS

2008/0065105 A1  3/2008 Larkin et al.
2009/0062604 A1  3/2009 Minosawa et al.
(Continued)

FOREIGN PATENT DOCUMENTS

EP    1989990 A1   11/2008
JP    3628742 B2    3/2005
(Continued)

OTHER PUBLICATIONS

Japanese Office Action dated May 31, 2016 in related Japanese Patent Application No. 2015-543719.
(Continued)

*Primary Examiner* — Ryan N Henderson
(74) *Attorney, Agent, or Firm* — Scully, Scott, Murphy & Presser, P.C.

(57) ABSTRACT

A medical manipulator includes: an insertion section having a main movable section and a distal end rigid section; a manipulator at which a treatment section is provided; an auxiliary movable section configured to move the treatment section; an imaging section configured to acquire an image in a field-of-vision range; a manipulation unit configured to output an instruction that specifies a position to which the treatment section is moved; a display configured to display the image; a determination unit configured to determine whether a condition is a partial movement condition or an entire movement condition when the determination unit receives the instruction; and a driving unit configured to drive the auxiliary movable section, the main movable section, and the imaging section based on determination of the determination unit.

12 Claims, 12 Drawing Sheets

Related U.S. Application Data

(60) Provisional application No. 61/757,427, filed on Jan. 28, 2013.

(51) Int. Cl.
  *A61B 1/018* (2006.01)
  *A61B 18/14* (2006.01)
  *A61B 34/30* (2016.01)
  *A61B 34/37* (2016.01)
  *A61B 90/00* (2016.01)

(52) U.S. Cl.
  CPC ...... *A61B 1/00087* (2013.01); *A61B 1/00131* (2013.01); *A61B 1/00133* (2013.01); *A61B 1/00147* (2013.01); *A61B 1/018* (2013.01); *A61B 1/31* (2013.01); *A61B 34/37* (2016.02); *A61B 90/37* (2016.02); *A61B 18/1492* (2013.01); *A61B 90/361* (2016.02); *A61B 2018/1412* (2013.01); *A61B 2018/1435* (2013.01); *A61B 2034/301* (2016.02)

(58) Field of Classification Search
  CPC ... A61B 1/00147; A61B 1/005; A61B 1/0051; A61B 1/008; A61B 1/01; A61B 1/018; A61B 1/31; A61B 34/30; A61B 34/32; A61B 34/35; A61B 34/37; A61B 34/70; A61B 34/71; A61B 34/72; A61B 34/74; A61B 2034/301–2034/306
  USPC ........ 600/102, 104, 106, 107, 114, 117, 118, 600/139–152; 604/528; 606/1
  See application file for complete search history.

(56) References Cited

U.S. PATENT DOCUMENTS

| | | | |
|---|---|---|---|
| 2009/0326556 A1* | 12/2009 | Diolaiti | A61B 1/00009 606/130 |
| 2010/0331856 A1 | 12/2010 | Carlson et al. | |
| 2011/0245844 A1 | 10/2011 | Jinno | |

FOREIGN PATENT DOCUMENTS

| | | |
|---|---|---|
| JP | 2006-312079 A | 11/2006 |
| JP | 2008-536552 A | 9/2008 |
| JP | 2009-262291 A | 11/2009 |
| JP | 4744595 B | 8/2011 |
| JP | 2011-206312 A | 10/2011 |
| JP | 2012-504017 A | 2/2012 |
| WO | 2006/110275 A2 | 10/2006 |
| WO | WO 2007-097034 A1 | 8/2007 |
| WO | WO 2010/039394 A1 | 4/2010 |

OTHER PUBLICATIONS

International Search Report dated Apr. 28, 2014 issued in PCT/JP2014/052370.

* cited by examiner

MEDICAL MANIPULATOR AND CONTROL METHOD OF MEDICAL MANIPULATOR

This application is a continuation application based on PCT Patent Application No. PCT/JP2014/052370, filed Jan. 28, 2014, whose priority is claimed on US Provisional Patent Application No. 61/757,427, filed Jan. 28, 2013. The contents of both the PCT Patent Application and the US Provisional patent application are incorporated herein by reference.

BACKGROUND OF THE INVENTION

Field of the Invention

The present invention relates to a medical manipulator used while inserted into a body cavity, and a control method of controlling the medical manipulator.

Description of Related Art

Recently, in order for a doctor to easily perform surgery, research on a medical treatment using a manipulator that can be deformed in various forms such as a bending motion, a moving motion, or the like, has been carried out. In order to reduce a stress on a patient during surgery, performing surgery after the introduction of an insertion section from an opening formed in a body wall into a body cavity or the like has been considered.

For example, an endoscopic surgical instrument disclosed in PCT International Publication No. WO 2007/097034 is constituted by a trocar for endoscopic surgery, a processor, a display, and a treatment tool.

The trocar is a guide member having a hollow shaft passing through a body wall. A connecting member is attached to a distal end section of the hollow shaft by a connecting pin. The connecting member has a telescopic structure including a main body section near the connecting pin and a slider slidably inserted into the main body section. As a protrusion amount of the slider with respect to the main body section is controlled, a length of the connecting member can be varied. An imaging device (an imaging section) is turnably attached to a distal end section of the slider by the connecting pin. An output signal of the imaging device is input into the processor.

The connecting member is turned about the connecting pin by a motor, an expansion/contraction amount of the connecting member is controlled, and the imaging device is turned about the connecting pin. The processor includes a signal processor configured to process a signal from the imaging device, a control circuit configured to calculate a protrusion amount or the like of the connecting member, and a driving circuit configured to drive the motor. The signal processor has an inclination detector configured to calculate an inclination amount of the hollow shaft when the hollow shaft is inclined about a substantial center of a portion thereof passing through the body wall as a support point. The control circuit calculates a turning amount and the expansion/contraction amount of the connecting member such that the imaging device is disposed at substantially the same position before and after the hollow shaft is inclined, using the inclination amount calculated by the inclination detector. The driving circuit swivels and expands/contracts the connecting member, and swivels the imaging device.

In the treatment tool, a rigid treatment tool insertion section extends from the manipulation unit manipulated by an operator such as a doctor or the like and is exchangeably inserted into the trocar. A treatment section such as a pair of gripping forceps is provided at a distal end of the treatment tool insertion section. A handle configured to open and close the pair of gripping forceps and a manipulation device such as a button or the like configured to manipulate the abovementioned motor are provided at the manipulation unit.

Effects of the endoscopic surgical instrument having the above-mentioned configuration are as follows. The operator manipulates the manipulation device to dispose the hollow shaft, the connecting member, and the imaging device on the same axis. These are inserted into the body cavity through the trocar. When the operator manipulates the manipulation unit and the hollow shaft is inclined using the body wall as a support point, the above-mentioned control circuit and driving circuit swivel the imaging device. For this reason, the imaging device can maintain a state in which the observation images are substantially matched on a display screen of the display while being affected little due to inclination of the hollow shaft.

SUMMARY OF THE INVENTION

According to a first aspect of the present invention, a medical manipulator includes: an insertion section configured to be inserted into a body and having a main movable section configured to be movable and a distal end rigid section provided closer to a distal end of the insertion section than the main movable section; a manipulator having a distal end section at which a treatment section is provided; an auxiliary movable section configured to move the treatment section with respect to the distal end rigid section with at least one degree of freedom; an imaging section configured to be movable with respect to the distal end rigid section and configured to acquire an image in a field-of-vision range; a manipulation unit configured to output an instruction that specifies a position to which the treatment section is moved; a display configured to display the image; a determination unit configured to determine whether a condition is a partial movement condition in which only moving the auxiliary movable section is required or an entire movement condition in which both of moving the auxiliary movable section and moving the main movable section are required, in order to move the treatment section to the position specified in the instruction when the determination unit receives the instruction; and a driving unit configured to drive the auxiliary movable section, the main movable section, and the imaging section based on the partial movement condition or the entire movement condition determined by the determination unit. The driving unit has a field-of-vision fixing mode in which, when the determination unit determines that the condition is the entire movement condition, the driving unit moves the auxiliary movable section and the main movable section so as to move the treatment section to the position specified in the instruction and the driving unit moves the imaging section such that a target area of a test object is projected in a reference area that forms a portion of the image.

According to a second aspect of the present invention, in the medical manipulator according to the first aspect, the auxiliary movable section may be provided closer to a proximal end of the manipulator than the treatment section. A proximal end section of the manipulator may be attached to the distal end rigid section.

According to a third aspect of the present invention, in the medical manipulator according to the first aspect, the auxiliary movable section may be provided at the insertion section. The manipulator may be inserted into a channel formed in the distal end rigid section so as to advance and retract.

According to a fourth aspect of the present invention, in the medical manipulator according to any one of the first aspect to the third aspect, the driving unit may move the imaging section based on a movement amount by which the main movable section is moved when the determination unit determines that the condition is the entire movement condition.

According to a fifth aspect of the present invention, in the medical manipulator according to any one of the first aspect to the fourth aspect, a size of the reference area may be capable of being varied.

According to a sixth aspect of the present invention, in the medical manipulator according to any one of the first aspect to the fifth aspect, the target area of the test object may be capable of being set by an operator.

According to a seventh aspect of the present invention, in the medical manipulator according to any one of the first aspect to the sixth aspect, the target area of the test object may be set to a portion of the test object projected to a center of the image when a confirmation instruction is input by an operator.

According to an eighth aspect of the present invention, in the medical manipulator according to any one of the first aspect to the seventh aspect, the driving unit may have a field-of-vision non-fixing mode in which, when the determination unit determines that the condition is the entire movement condition, the driving unit moves the auxiliary movable section and the main movable section so as to move the treatment section to the position specified in the instruction and the driving unit does not automatically move the imaging section. The driving unit may be configured to be set to one of the field-of-vision fixing mode and the field-of-vision non-fixing mode and may be configured to be capable of being switched from the one of the field-of-vision fixing mode and the field-of-vision non-fixing mode to another of the field-of-vision fixing mode and the field-of-vision non-fixing mode.

According to a ninth aspect of the present invention, in the medical manipulator according to any one of the first aspect to the eighth aspect, the driving unit may move the imaging section based on the image when the determination unit determines that the condition is the entire movement condition.

According to a tenth aspect of the present invention, in the medical manipulator according to any one of the first aspect to the ninth aspect, the instruction output from the manipulation unit may specify a position and an orientation to which the treatment section is moved. The determination unit may determine whether the condition is the partial movement condition or the entire movement condition by moving the treatment section to the position and the orientation specified in the instruction. The driving unit may move the treatment section to the position and the orientation specified in the instruction.

According to an eleventh aspect of the present invention, a control method of controlling a medical manipulator including: an insertion section configured to be inserted into a body and having a main movable section configured to be movable and a distal end rigid section provided closer to a distal end of the insertion section than the main movable section; a manipulator having a distal end section at which a treatment section is provided; an auxiliary movable section configured to move the treatment section with respect to the distal end rigid section with at least one degree of freedom; an imaging section configured to be movable with respect to the distal end rigid section and configured to acquire an image in a field-of-vision range; and a manipulation unit configured to output an instruction that specifies a position to which the treatment section is moved, includes: when the instruction is received, determining whether a condition is a partial movement condition in which only moving the auxiliary movable section is required or an entire movement condition in which both of moving the auxiliary movable section and the main movable section are required in order to move the treatment section to the position specified in the instruction; when the condition is determined as the partial movement condition, moving the auxiliary movable section without moving the main movable section and moving the treatment section to the position specified in the instruction; and when the condition is determined as the entire movement condition, with moving the auxiliary movable section and the main movable section and moving the treatment section to the position specified in the instruction, moving the imaging section such that a target area of a test object is projected in a reference area that forms a portion of the image.

According to a twelfth aspect of the present invention, the control method of controlling the medical manipulator according to the eleventh aspect may further include, when the condition is determined as the entire movement condition, moving the imaging section based on a movement amount by which the main movable section is moved.

DETAILED DESCRIPTION OF THE INVENTION

First Embodiment

Hereinafter, a medical manipulator according to a first embodiment of the present invention is described with reference to FIGS. 1 to 13.

Figure 1:
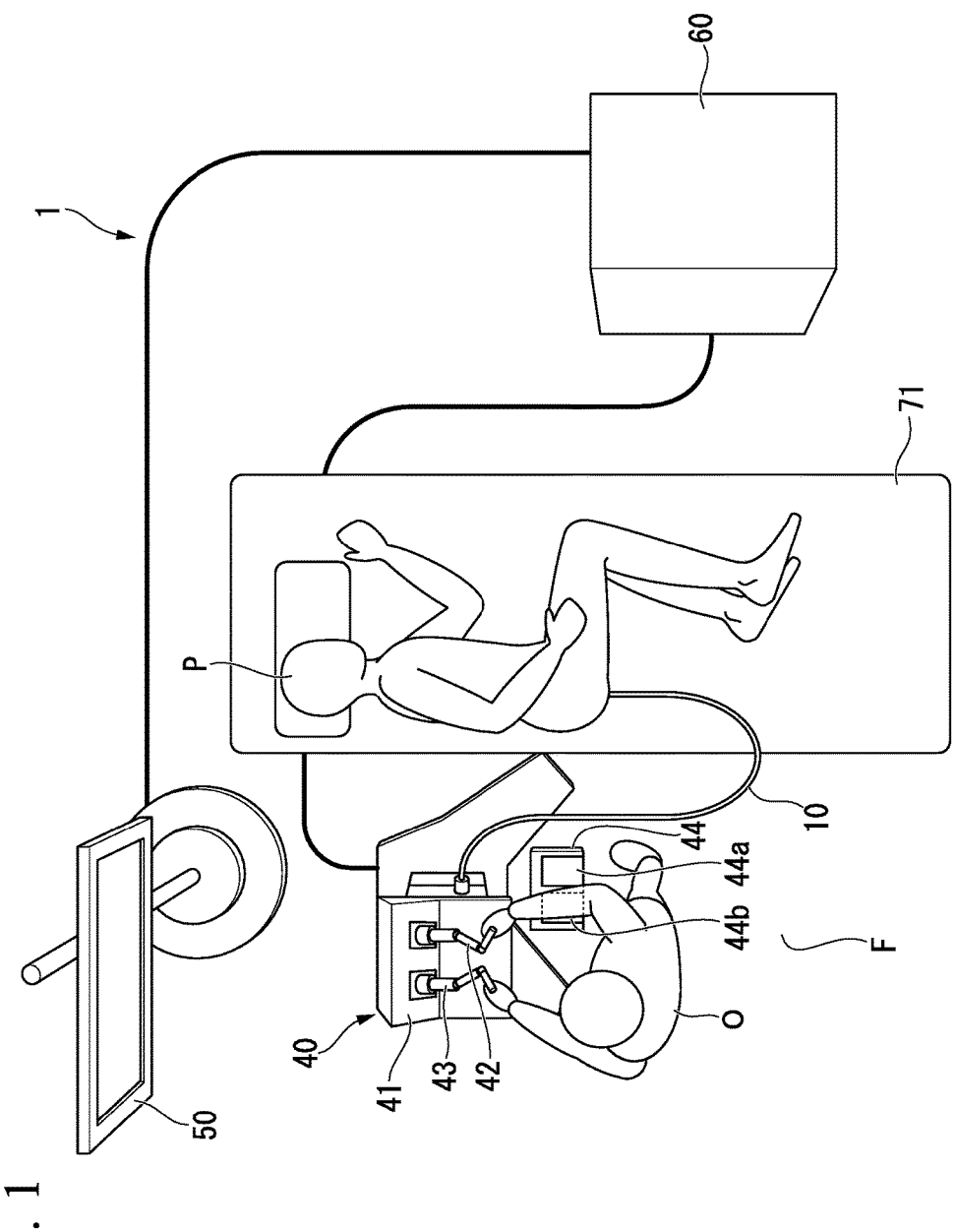
FIG. 1 is a general view showing a medical manipulator according to a first embodiment of the present invention.
Figure 2:
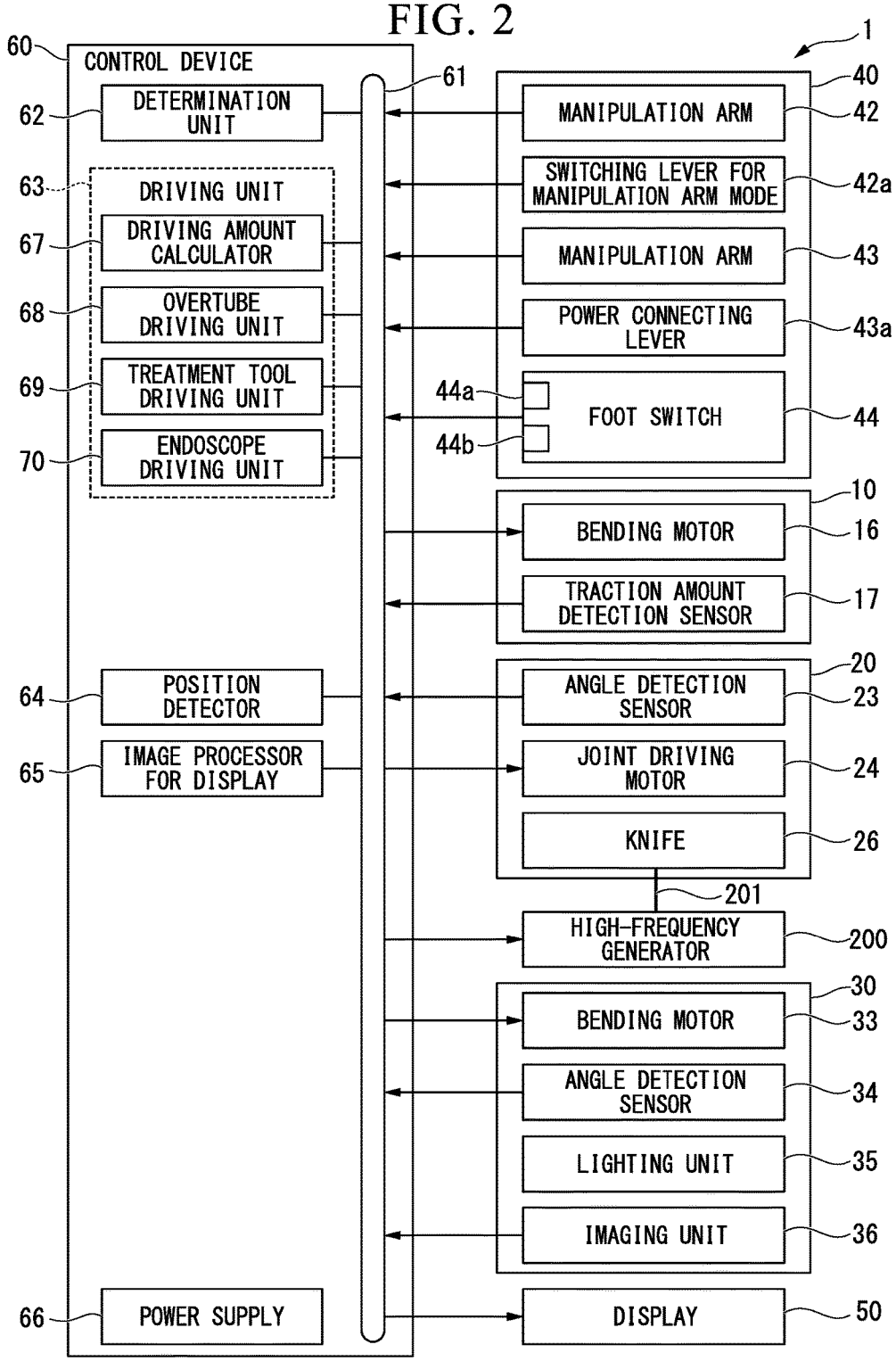
FIG. 2 is a block diagram of the medical manipulator according to the first embodiment of the present invention.
Figure 3:
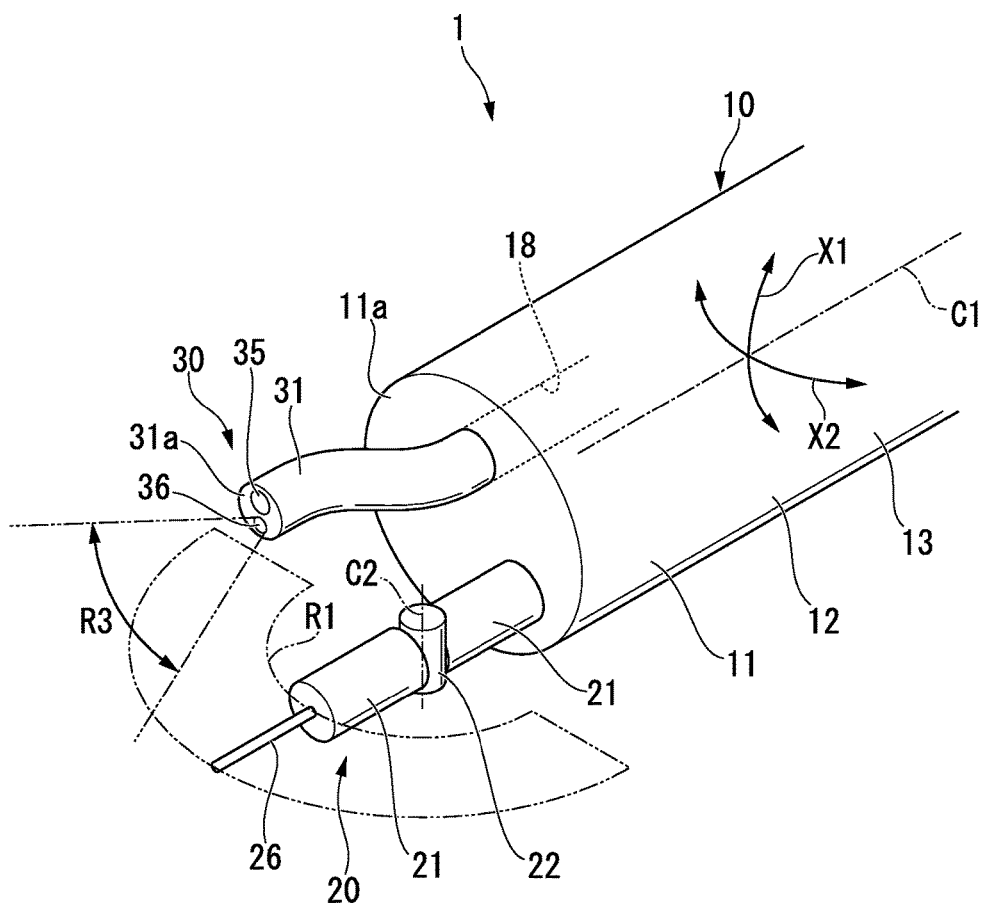
FIG. 3 is a perspective view of a distal end section of an overtube of the medical manipulator according to the first embodiment of the present invention.

As shown in FIGS. 1 to 3, a medical manipulator 1 according to the embodiment includes an overtube (an insertion section) 10, a treatment tool (a manipulator) 20, an endoscope (an imaging section) 30, a manipulation unit 40, a display 50, and a control device 60. The overtube 10 is inserted into a body. A proximal end section of the treatment tool 20 is attached to a distal end rigid section 11 disposed at a distal end of the overtube 10. The endoscope 30 is configured to be movable with respect to the distal end rigid section 11. The manipulation unit 40 is manipulated by an operator O such as a doctor or the like to output a manipulation instruction (an instruction). The display 50 displays an image acquired by the endoscope 30. The control device 60 controls the overtube 10, the treatment tool 20, and the endoscope 30 in accordance with the manipulation instruction.

The overtube 10 has flexibility. As show in FIG. 3, the overtube 10 has the above-mentioned distal end rigid section 11, a bending section (a main movable section) 12, and a flexible tube section 13. The bending section 12 is provided closer to a proximal end of the overtube 10 than the distal end rigid section 11 and is configured to be bendable. The flexible tube section 13 is provided closer to the proximal end than the bending section 12 and has flexibility.

The distal end rigid section 11 is formed of a metal such as stainless steel or the like in a columnar shape. The proximal end section of the above-mentioned treatment tool 20 is attached to a distal end surface 11a of the distal end rigid section 11.

A mechanism having a known configuration may be used as the bending section 12. While not shown, the bending section 12 includes a plurality of joint rings turnably connected to each other, and the plurality of joint rings are arranged in parallel in a direction of an axis C1 of the overtube 10. Distal end sections of four manipulation wires are connected to the joint ring close to the distal end among the plurality of joint rings at equal angle intervals around the axis C1. Proximal end sections of the manipulation wires are respectively connected to bending motors 16 (see FIG. 2) provided at a proximal end section of the overtube 10. As the proximal end sections of the manipulation wires are pulled by the bending motors 16 in the direction of the axis C1, the bending section 12 can be bent in a direction X1 and a direction X2 perpendicular to the axis C1 shown in FIG. 3. The direction X1 and the direction X2 are perpendicular to each other. In this way, the bending section 12 has two degrees of freedom.

A movement amount of the manipulation wire in the direction of the axis C1 is detected by a traction amount detection sensor 17 (see FIG. 2). The traction amount detection sensor 17 converts the detected movement amount into a signal to output the signal to the control device 60.

As shown in FIG. 3, a channel 18 is formed in the overtube 10. The channel 18 has an opening at the distal end surface 11a and extends in the direction of the axis C1 of the overtube 10.

The treatment tool 20 includes a plurality of tubular bodies 21 disposed in parallel in a longitudinal direction of the treatment tool 20. The treatment tool 20 is configured such that the adjacent tubular bodies 21 in the longitudinal direction are connected by a joint section (an auxiliary movable section) 22. As an example, the tubular body 21 and the joint section 22 are formed of a material having an insulating property such as ceramics or the like. As shown in FIG. 2, an angle detection sensor 23 and a joint driving motor 24 are provided in the joint section 22. The angle detection sensor 23 detects an angle formed by the adjacent tubular bodies 21 around an axis C2 (see FIG. 3) of the joint section 22. The angle detection sensor 23 is, for example, an encoder, a potentiometer, or the like. The joint driving motor 24 adjusts the angle. The angle detection sensor 23 converts the detected angle into a signal to output the signal to the control device 60. The joint driving motor 24 is driven by the control device 60. That is, as a knife 26 is turned by the joint driving motor 24, the knife 26 can be moved with respect to the distal end rigid section 11 with one degree of freedom.

As shown in FIG. 3, a proximal end section of the knife (a treatment section) 26 formed in a rod shape is fixed to the tubular body 21 disposed at the distal end side. The knife 26 can be formed of a metal having biocompatibility such as stainless steel or the like.

One end section of a wiring 201 shown in FIG. 2 is connected to the proximal end section of the knife 26. The wiring 201 is disposed in the tubular body 21 and the joint section 22. The other end section of the wiring 201 is connected to a high-frequency generator 200 that can output a high-frequency current. The high-frequency generator 200 is connected to the control device 60. The high-frequency generator 200 outputs a high-frequency current in accordance with the control of the control device 60.

As the joint driving motor 24 is driven, the knife 26 turns around the axis C2 with respect to the distal end rigid section 11, and can be moved within a range R1 shown in FIG. 3 defined on a reference plane.

In the embodiment, an example in which the treatment tool 20 includes one joint section 22 is described for the convenience of description. However, the number of joint sections 22 included in the treatment tool 20 is not limited, and the treatment tool 20 may include two or more joint sections 22. In this case, the manipulator has a multi joint structure. For this reason, the knife 26 can be moved with respect to the distal end rigid section 11 with two degrees of freedom or more. Like the above-mentioned bending section 12, the treatment tool 20 may be configured such that the plurality of joint rings (segments) are turnably connected.

While not shown in detail, in the endoscope 30, the multi joint structure constituted by the above-mentioned plurality of joint rings is provided in an imaging section main body 31 formed of a flexible material such as silicon or the like in a columnar shape. The distal end section of the manipulation wire (not shown) is connected to the joint ring close to the distal end among the plurality of joint rings. A driving shaft of a bending motor 33 shown in FIG. 2 is connected to the proximal end section of the manipulation wire. A number of revolutions of the driving shaft of the bending motor 33 is detected by an angle detection sensor 34. The number of revolutions detected by the angle detection sensor 34 is output to the control device 60.

A lighting unit 35 having an LED, and an imaging unit 36 having a CCD or the like are provided at a distal end surface 31*a* of the imaging section main body 31 while the lighting unit 35 and the imaging unit 36 are exposed to the outside. The lighting unit 35 illuminates a forward side of the endoscope 30 by receiving power from a power supply 66 (to be described below). The imaging unit 36 can acquire an image in a predetermined field-of-vision range R3 defined in front of the endoscope 30. The imaging unit 36 converts the image into a signal to output the signal to the control device 60.

The endoscope 30 is inserted into the channel 18 of the overtube 10 and is maintained in a state in which a distal end section of the endoscope 30 protrudes from the distal end rigid section 11 toward a forward side thereof. A plurality of joint rings are also provided in a portion of the imaging section main body 31 protruding from the distal end rigid section 11 toward the forward side thereof. As the bending motor 33 is driven to advance and retract the manipulation wire, the imaging section main body 31 protruding from the distal end rigid section 11 toward the forward side thereof can be bent in a predetermined shape.

As shown in FIGS. 1 and 2, the manipulation unit 40 has a pair of manipulation arms 42 and 43 attached to a manipulation table 41, and a foot switch 44 disposed on a floor F.

The manipulation arms 42 and 43 have a multi joint structure. The manipulation arm 42 is configured to manipulate the bending section 12 of the overtube 10 to be bent, and manipulate a position and an orientation (a direction) of the knife 26 of the treatment tool 20. The manipulation arm 43 is configured to manipulate the endoscope 30 to be bent. When the manipulation arms 42 and 43 are manipulated, the manipulation instruction is output to the control device 60.

A switching lever 42*a* for a manipulation arm mode shown in FIG. 2 is provided at a distal end section of the manipulation arm 42. As the switching lever 42*a* is manipulated, a manipulation arm mode switching signal is output to a driving amount calculator 67 (to be described below) of the control device 60. Accordingly, a manipulation arm control mode of the driving amount calculator 67 is switched between a bending section manipulation mode and a knife manipulation mode. In the bending section manipulation mode, a target controlled by the manipulation arm 42 is the bending section 12 of the overtube 10. In the knife manipulation mode, the target controlled by the manipulation arm 42 is the knife 26 of the treatment tool 20.

A power connecting lever 43*a* configured to output a high-frequency current from the above-mentioned high-frequency generator 200 is provided at a distal end section of the manipulation arm 43.

The foot switch 44 includes a changeover switch 44*a* for an imaging section control mode and a confirmation switch 44*b*. The changeover switch 44*a* is used to switch the imaging section control mode of the driving amount calculator 67 (to be described below). The confirmation switch 44*b* is used to allow the operator O to input a confirmation instruction or the like. As the changeover switch 44*a* is manipulated, an imaging section control mode switching signal is output to the driving amount calculator 67. Accordingly, the imaging section control mode of the driving amount calculator 67 is switched between a field-of-vision fixing mode and a field-of-vision non-fixing mode. In the field-of-vision fixing mode, the endoscope 30 can be automatically manipulated to be bent. In the field-of-vision non-fixing mode, the endoscope 30 cannot be automatically manipulated to be bent.

As shown in FIG. 1, the display 50 is disposed at a position opposite to the operator O when the manipulation arms 42 and 43 are gripped by his/her hands. The display 50 is connected to the control device 60.

As shown in FIG. 2, the control device 60 has a determination unit 62, a driving unit 63, a position detector 64, an image processor 65 for display, and the power supply 66. The determination unit 62, the driving unit 63, the position detector 64, and the image processor 65 are connected to a bus 61. The bending motor 16 and the traction amount detection sensor 17 of the overtube 10, the angle detection sensor 23 and the joint driving motor 24 of the treatment tool 20, the bending motor 33, the angle detection sensor 34, and the imaging unit 36 of the endoscope 30, the manipulation arms 42 and 43, the switching lever 42*a*, the power connecting lever 43*a*, and the foot switch 44 of the manipulation unit 40, and the display 50 are connected to the bus 61.

Each of the determination unit 62, the driving unit 63, the position detector 64, and the image processor 65 is constituted by a calculation element, a memory, a control program, and so on. Hereinafter, first, the position detector 64 is described.

A table showing a bending amount of the bending section 12 with respect to a movement amount of the manipulation wire, a length of the distal end rigid section 11 of the overtube 10, a length of the tubular body 21 of the treatment tool 20, a length of the knife 26 of the treatment tool 20, a length of the joint ring of the endoscope 30, a direction of the field-of-vision range R3 with respect to the lighting unit 35, and so on, are stored in the memory of the position detector 64.

The calculation element of the position detector 64 calculates the bending amount of the bending section 12 and a movement amount of the distal end surface 11*a* of the overtube 10 based on the movement amount detected by the traction amount detection sensor 17, the table stored in the memory, and so on. The calculation element of the position detector 64 calculates a shape of the treatment tool 20, a position of the knife 26 of the treatment tool 20 with respect to the distal end surface 11*a* of the overtube 10, and so on, based on the angle detected by the angle detection sensor 23 of the treatment tool 20 and the values stored in the memory. The calculation element of the position detector 64 calculates a shape of the endoscope 30, a position of the distal end surface 31*a* of the endoscope 30 with respect to the distal end surface 11*a* of the overtube 10, and so on, based on the angle detected by the angle detection sensor 34 of the endoscope 30 and the values stored in the memory. The calculation element of the position detector 64 calculates the field-of-vision range R3 with respect to the distal end surface 11*a* of the overtube 10 based on the position of the distal end surface 31*a* and the values stored in the memory.

A driving amount detector configured to detect the position of the knife 26 and the position of the distal end surface 31*a* of the endoscope 30 is constituted by the angle detection sensors 23 and 34 and the position detector 64.

As shown in FIG. 2, the driving unit 63 includes the driving amount calculator 67, an overtube driving unit 68, a treatment tool driving unit 69 and an endoscope driving unit 70.

As described above, the driving amount calculator 67 has the bending section manipulation mode and the knife manipulation mode in the manipulation arm control mode. The driving amount calculator 67 has the field-of-vision fixing mode and the field-of-vision non-fixing mode in the imaging section control mode.

The driving amount calculator 67 recognizes the manipulation instruction output from the manipulation arm 42 as an instruction to bend the bending section 12 of the overtube 10 when the manipulation arm control mode is the bending section manipulation mode. The driving amount calculator 67 outputs a signal specifying the bending motor 16 to be driven and the driving amount thereof to the overtube driving unit 68 based on the manipulation instruction.

Meanwhile, the driving amount calculator 67 recognizes the manipulation instruction output from the manipulation arm 42 as an instruction showing a position and an orientation to which the knife 26 is moved when the manipulation arm control mode is the knife manipulation mode.

The driving amount calculator 67 calculates the driving amount of the joint driving motor 24 through known inverse kinematics calculation and so on when the determination unit 62 determines that the condition is a partial movement condition as described below. The partial movement condition is a condition in which, when the knife 26 is moved based on the manipulation instruction, the knife 26 can be moved by only turning the joint section 22 of the treatment tool 20 without bending the bending section 12 of the overtube 10. The driving amount calculator 67 outputs a signal specifying the calculated driving amount of the joint driving motor 24 to the treatment tool driving unit 69.

On the other hand, when the determination unit 62 determines that the condition is the entire movement condition, the driving amount calculator 67 calculates driving amounts of the joint driving motor 24 and the bending motor 16 through inverse kinematics calculation. The entire movement condition is a condition in which, when the knife 26 is moved based on the manipulation instruction, both of turning the joint section 22 of the treatment tool 20 and bending the bending section 12 of the overtube 10 are required. The driving amount calculator 67 outputs signals specifying the calculated driving amounts of the joint driving motor 24 and the bending motor 16 to the treatment tool driving unit 69 and the endoscope driving unit 70, respectively. Here, when the above-mentioned imaging section control mode is the field-of-vision non-fixing mode, the endoscope 30 is not automatically bent. When the imaging section control mode is the field-of-vision fixing mode, the endoscope 30 is automatically bent depending on the condition.

The overtube driving unit 68, the treatment tool driving unit 69, and the endoscope driving unit 70 are drivers configured to drive the bending motor 16 of the overtube 10, the joint driving motor 24 of the treatment tool 20, and the bending motor 33 of the endoscope 30, respectively. The overtube driving unit 68, the treatment tool driving unit 69, and the endoscope driving unit 70 drive the bending motor 16, the joint driving motor 24, and the bending motor 33 based on the signals output from the driving amount calculator 67, respectively.

The determination unit 62 acquires the position and orientation to which the knife 26 recognized by the driving amount calculator 67 is moved, when the imaging section control mode of the driving amount calculator 67 is the field-of-vision fixing mode and the manipulation arm control mode is the knife manipulation mode. The determination unit 62 determines whether the condition is the partial movement condition in which only turning the joint section 22 of the treatment tool 20 is required or the entire movement condition in which both of turning the joint section 22 of the treatment tool 20 and bending the bending section 12 of the overtube 10 are required, in order to move the knife 26 to match the position and orientation of the knife 26 with the command values of the acquired position and orientation, through inverse kinematics calculation. The determination unit 62 outputs the determined movement condition to the driving amount calculator 67. That is, in the case of the manipulation instruction to move the knife 26 with respect to the distal end rigid section 11 within the range R1, for example, when the manipulation amount of the manipulation arm 42 is relatively small, the determination unit 62 determines that the condition is the partial movement condition. The driving amount calculator 67 turns the joint section 22 of the treatment tool 20 by the treatment tool driving unit 69 without bending the bending section 12. Meanwhile, in the case of the manipulation instruction of moving the knife 26 with respect to the distal end rigid section 11 beyond the range R1, for example, when the manipulation amount of the manipulation arm 42 is relatively large, the determination unit 62 determines that the condition is the entire movement condition. The driving amount calculator 67 bends the bending section 12 of the overtube 10 while turning the joint section 22 of the treatment tool 20 by the treatment tool driving unit 69 and the endoscope driving unit 70.

The image processor 65 appropriately converts the image signal output from the imaging unit 36 to output the converted image signal to the display 50.

The power supply 66 supplies the power input from the outside to the overtube 10, the treatment tool 20, the endoscope 30, the manipulation unit 40, the display 50, the determination unit 62 of the control device 60, and so on.

Next, surgery using the medical manipulator 1 according to the embodiment having the above-mentioned configuration is described focusing on a control method of the medical manipulator 1 used when the knife 26 is moved. Hereinafter, while the case in which a target tissue formed in an inner wall of the large intestine (a test object) is treated is described, the target area is not limited thereto. For example, the target area may be a hollow organ such as the esophagus, the stomach, the duodenum, the small intestine, the uterus, the bladder, and so on.

As shown in FIG. 1, an assistant (not shown) lays a patient P on a surgical table 71 beside which the manipulation unit 40 is disposed, and performs appropriate treatment such as sterilization, anesthesia, and so on. When the medical manipulator 1 is started, power is supplied from the power supply 66 to the overtube 10, the treatment tool 20, the endoscope 30, the manipulation unit 40, the display 50, the determination unit 62 of the control device 60, and so on.

Figure 4:
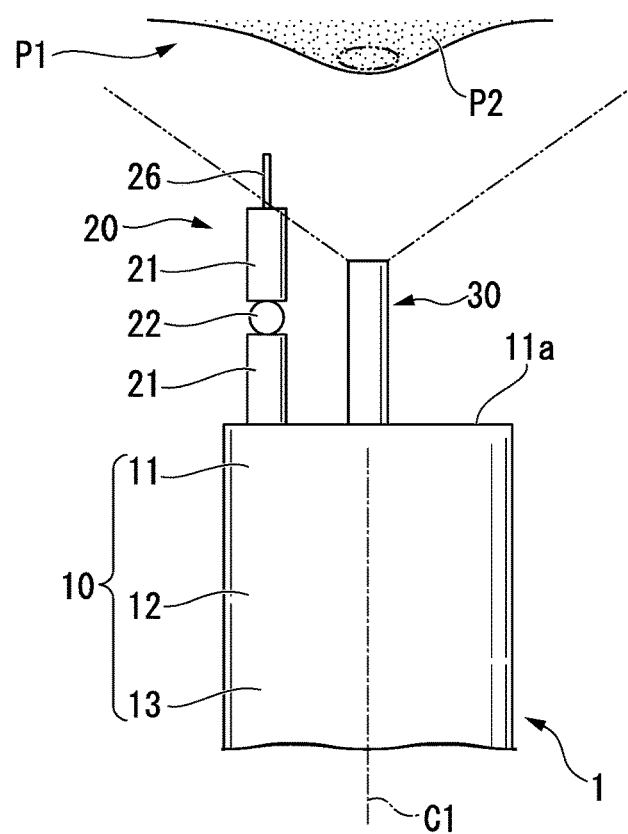
FIG. 4 is a view showing a state in which a distal end surface of the overtube is opposite to a target tissue.

The operator O manipulates the changeover switch 44a of the foot switch 44 to switch the imaging section control mode to the field-of-vision non-fixing mode. The operator O manipulates the switching lever 42a to switch the manipulation arm control mode to the knife manipulation mode. The operator O manipulates the manipulation arm 42 to deform the treatment tool 20 in a straight shape along the axis C1 as shown in FIG. 4. The operator O manipulates the manipulation arm 43 to deform the endoscope 30 in a straight shape along the axis C1.

The operator O manipulates the switching lever 42a to switch the manipulation arm control mode to the bending section manipulation mode. The operator O manipulates the changeover switch 44a of the foot switch 44 to switch the imaging section control mode to the field-of-vision fixing mode.

The operator O illuminates a forward side of the endoscope 30 by supplying power from the power supply 66 to the imaging unit 36. The operator O grips the manipulation arms 42 and 43 and checks the image in front of the endoscope 30 acquired by the imaging unit 36 through the display 50.

The operator O instructs the assistant to introduce the overtube 10 into the large intestine P1 from the anus of the patient P as shown in FIG. 4. When the operator O manipulates the manipulation arm 42 to bend the bending section 12 of the overtube 10, the manipulation instruction is output from the manipulation arm 42. In the driving amount calculator 67, since the manipulation arm control mode is the bending section manipulation mode, the bending motor 16 is driven based on the manipulation instruction, and the bending section 12 is bent. Accordingly, a direction of the distal end surface 11a of the overtube 10 and directions of the treatment tool 20 and the endoscope 30 protruding forward from the distal end surface 11a are varied with respect to the flexible tube section 13 of the overtube 10.

Figure 5:
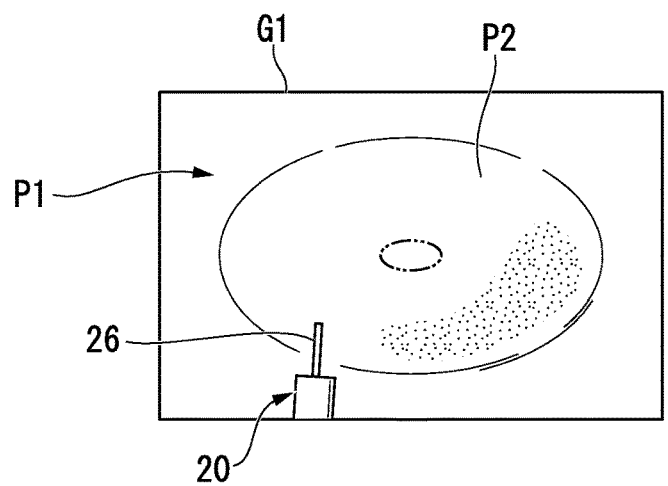
FIG. 5 is a view showing an example of an image displayed on a display when the distal end surface of the overtube is opposite to the target tissue.

The operator O instructs the assistant to stop introduction of the overtube 10 when the distal end surface 11a of the overtube 10 is opposite to a target tissue P2 in the large intestine P1. The operator O adjusts a distance between the target tissue P2 of the large intestine P1 and the distal end surface 11a to a predetermined value. Here, the image G1 on which the target tissue P2 of the large intestine P1 is projected as shown in FIG. 5 is displayed on the display 50.

The operator O operates the switching lever 42a to switch the manipulation arm control mode to the knife manipulation mode. Here, for example, when the operator O manipulates the manipulation arm 42 by a relatively small manipulation amount in which the knife 26 is moved within the range R1 as described above, the manipulation instruction output from the manipulation arm 42 is recognized as the position and orientation to which the knife 26 is moved by the driving amount calculator 67.

The determination unit 62 determines whether the condition is the partial movement condition or the entire movement condition in order to move the knife 26 to match the position and orientation of the knife 26 with the command values of the acquired position and orientation through the inverse kinematics calculation (a movement condition determination process). In this case, the determination unit 62 determines that the condition is the partial movement condition in which the manipulation amount of the manipulation arm 42 is relatively small, that is, only turning the joint section 22 is required, without bending the bending section 12.

Figure 6:
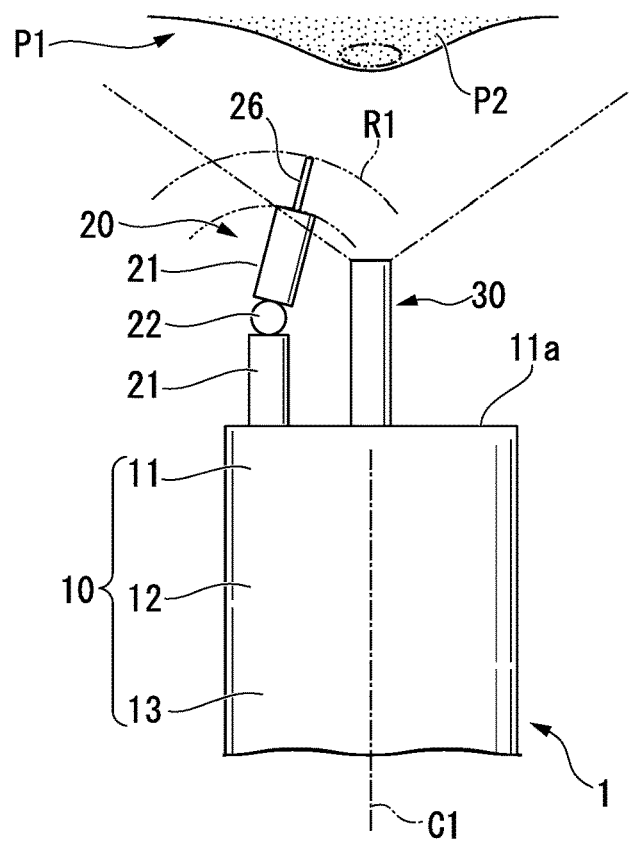
FIG. 6 is a view showing a state in which a joint section of a treatment tool of the medical manipulator according to the first embodiment of the present invention is bent.
Figure 7:
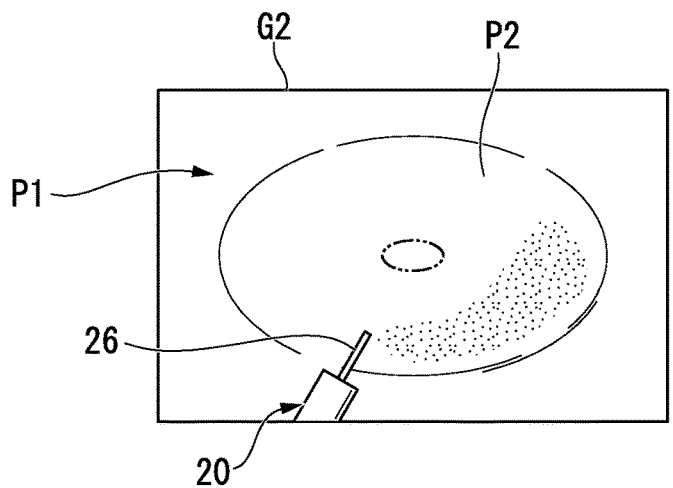
FIG. 7 is a view showing an example of an image displayed on the display when the joint section of the treatment tool is bent.

The driving amount calculator 67 of the driving unit 63 to which the movement condition is output as the partial movement condition from the determination unit 62 drives the joint driving motor 24 using the treatment tool driving unit 69. As shown in FIG. 6, the driving amount calculator 67 turns the joint section 22 only and moves the knife 26 to the position and orientation specified in the manipulation instruction using the joint driving motor 24, without bending the bending section 12 (a partial movement process). Here, since the endoscope 30 is not moved, as shown in FIG. 7, an image G2 in which the treatment tool 20 is relatively slightly moved with respect to the target tissue P2 with no movement of the target tissue P2 is displayed on the display 50.

Meanwhile, for example, the operator O manipulates the manipulation arm 42 by a relatively large manipulation amount in which the knife 26 is moved beyond the range R1 as described above from a state in which the treatment tool 20 is in a straight shape. In this case, in the above-mentioned movement condition determination process, the determination unit 62 determines that the condition is the entire movement condition in which the manipulation amount of the manipulation arm 42 is relatively large, that is, both of turning the joint section 22 and bending the bending section 12 of the overtube 10 are needed.

Figure 8:
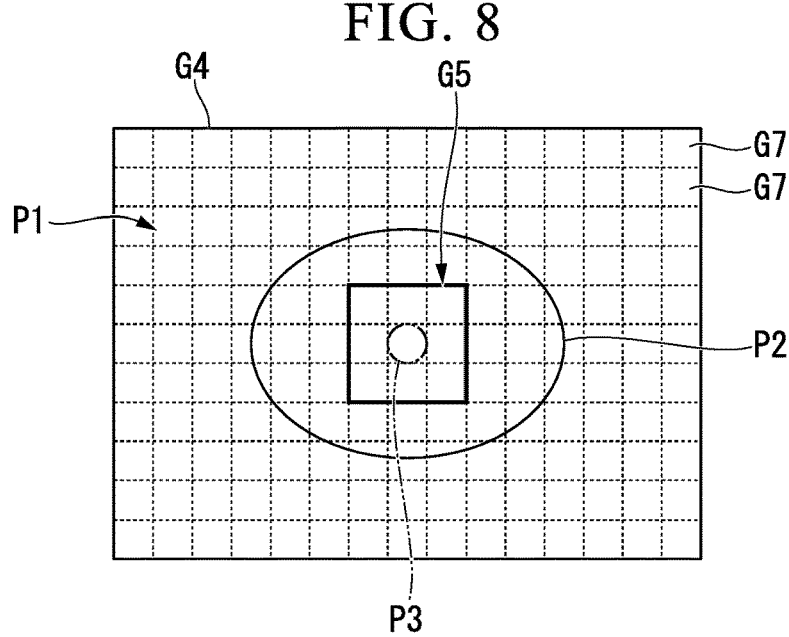
FIG. 8 is a view showing a positional relationship between a reference area and a target area in an image acquired by the medical manipulator according to the first embodiment of the present invention.
Figure 12:
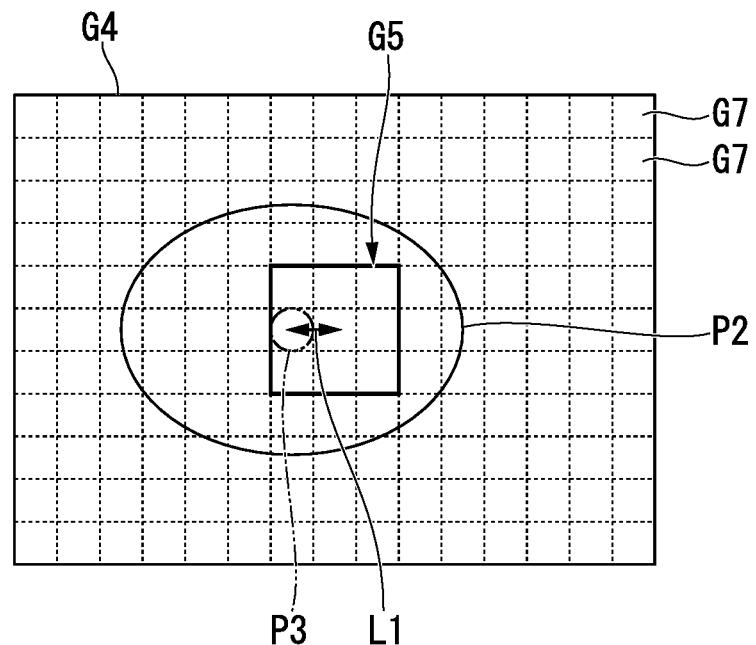
FIG. 12 is a view showing a state in which the target area is moved with respect to the reference area in the image acquired by the medical manipulator according to the first embodiment of the present invention.

When the determination unit 62 determines that the condition is the entire movement condition, the driving amount calculator 67 automatically sets a portion of the large intestine P1 projected to a central part of a reference area G5 that forms a portion of an image G4 shown in FIG. 8 acquired by the imaging unit 36 as a target area P3. In FIG. 8, pixels G7 that constitute the image G4 are shown. In FIGS. 8 and 12 (to be described below), the treatment tool 20 is not shown. The reference area G5 is constituted by nine pixels G7 configured in a rectangular shape as a whole. The reference area G5 is set to a central part of the image G4.

Figure 9:
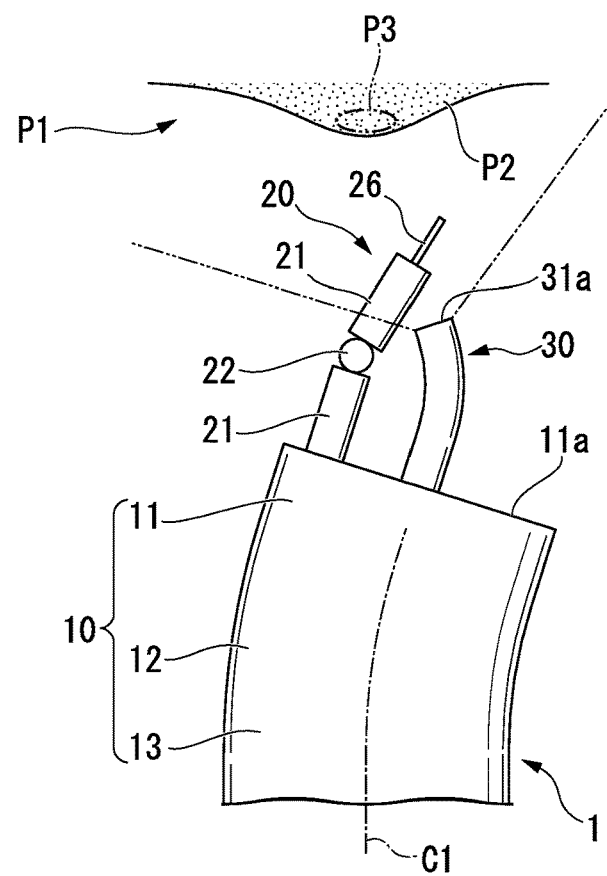
FIG. 9 is a view showing a state in which the joint section of the treatment tool and an endoscope are bent.

The driving amount calculator 67 drives the joint driving motor 24 and the bending motor 16 using the treatment tool driving unit 69 and the overtube driving unit 68 to turn the joint section 22 and bend the bending section 12 as shown in FIG. 9. Accordingly, the driving amount calculator 67 moves the knife 26 to the position and orientation specified in the manipulation instruction. Simultaneously, as shown in FIG. 8, the driving amount calculator 67 bends the endoscope 30 such that the target area P3 of the large intestine P1 is projected in the reference area G5 (an entire movement process).

When the bending section 12 is bent, a portion of the endoscope 30 in the vicinity of the distal end surface 11a is also moved as shown in FIG. 9. As the endoscope 30 is bent such that the distal end surface 31a is opposite to the target area P3, the image G4 can be adjusted such that a portion of the target area P3 of the large intestine P1 projected in the image G4 does not depart from the reference area G5. In the embodiment, the movement amount of the manipulation wire is detected by the traction amount detection sensor 17. A relationship between the movement amount of the manipulation wire and the bending amount of the bending section 12 is stored in the position detector 64. The driving amount calculator 67 calculates the bending amount of the bending section 12 of the overtube 10 from these movement amounts and the table. As a distance between the target tissue P2 and the distal end surface 11a becomes a predetermined value, the driving amount calculator 67 can make an adjustment such that the target area P3 in the image G4 does not depart from the reference area G5.

Figure 10:
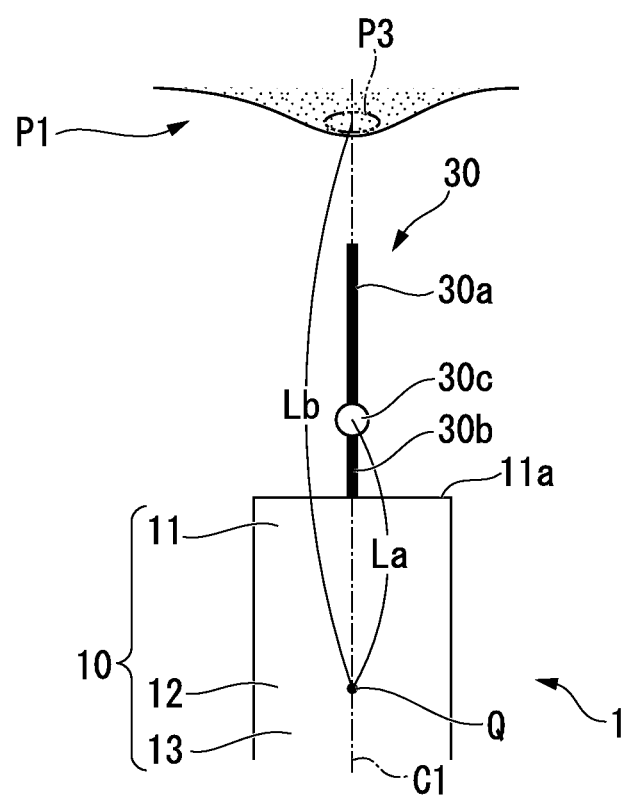
FIG. 10 is a view in which the endoscope or the like of the medical manipulator according to the first embodiment of the present invention is modeled.

Here, an angle to which the endoscope 30 is bent is described using a model in which the medical manipulator 1 shown in FIG. 10 is simplified.

Figure 11:
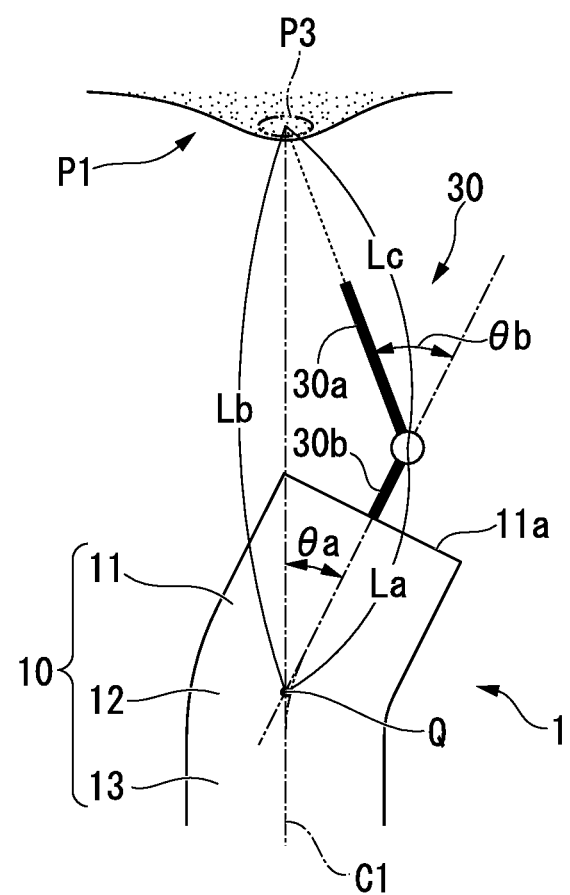
FIG. 11 is a view for describing a bent angle of the endoscope when the endoscope or the like of the medical manipulator according to the first embodiment of the present invention is modeled.

The endoscope 30 formed in the straight shape and the target area P3 of the large intestine P1 are disposed on the axis C1 of the overtube 10. The endoscope 30 is configured by connecting adjacent joint rings 30a and 30b in the longitudinal direction using a pin 30c. In FIGS. 10 and 11, the joint rings 30a and 30b are shown in a rod shape. A proximal end section of the joint ring 30b is attached to the distal end surface 11a of the overtube 10. That is, the endoscope 30 of the model has one degree of freedom.

Here, a length from the pin 30c to a bending center Q of the bending section 12 is La, and a length from the target area P3 to the bending center Q is Lb.

In a state in which a position of the flexible tube section 13 with respect to the target area P3 is fixed, as shown in FIG. 11, the bending section 12 is bent to an angle θa. Here, a length Lc from the target area P3 to the pin 30c and an angle θb to which the pin 30c is turned such that a distal end of the joint ring 30a is opposite to the target area P3 are expressed as Equation 1 and Equation 2. A unit of the angles θa and θb is radians.

$$Lc = \sqrt{La^2 + Lb^2 - 2LaLb\cos\theta a} \quad \text{(Equation 1)}$$

$$\theta b = \pi - \frac{Lb}{Lc}\sin^{-1}\theta a \quad \text{(Equation 2)}$$

When the bending section 12 of the overtube 10 is bent without bending the endoscope 30, in the image G4 shown in FIG. 8, the target area P3 and the target tissue P2 are moved as shown in FIG. 12. In the embodiment, as the endoscope 30 is bent based on the movement amount of the manipulation wire, the target area P3 is moved to the central part of the reference area G5 as shown in FIG. 8.

Figure 13:
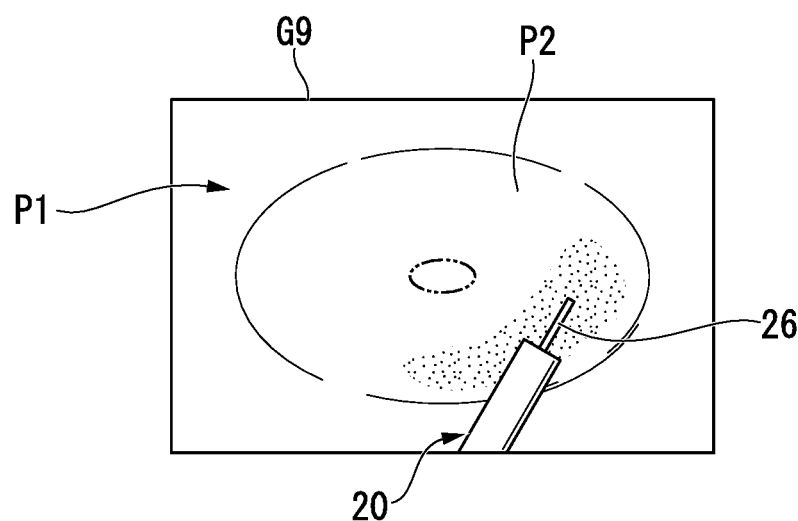
FIG. 13 is a view showing an example of the image displayed on the display when the treatment tool and the endoscope are bent.

In the entire movement process, when the endoscope 30 is bent simultaneously while the joint section 22 is turned and the bending section 12 is bent, an image G9 as shown in FIG. 13 is displayed on the display 50. That is, while the treatment tool 20 is relatively largely moved with respect to the target tissue P2, projection to the center of the image G9 before and after turning the joint section 22 and so on is not varied.

Accordingly, the control method of the medical manipulator 1 according to the embodiment is terminated. After that, as necessary, the operator O manipulates the manipulation arm 43 to bend the endoscope 30, and adjusts the field-of-vision range R3. The operator O manipulates the power connecting lever 43a to output the high-frequency current from the high-frequency generator 200. The operator O manipulates the manipulation arm 42 and brings the knife 26 in contact with the target tissue P2 to incise the target tissue P2.

In the case in which the endoscope 30 is not automatically bent when the manipulation arm control mode is switched to the knife manipulation mode, the changeover switch 44a is manipulated to switch the imaging section control mode to the field-of-vision non-fixing mode.

The operator O deforms the treatment tool 20 and the endoscope 30 in a straight shape along the axis C1. The operator O instructs the assistant to extract the overtube 10 from the large intestine P1. After that, the operator O performs necessary treatment, and a series of surgical procedure is terminated.

According to the medical manipulator 1 and the control method of the medical manipulator 1 according to the embodiment, in the case in which the manipulation unit 40 is manipulated to move the knife 26 within the range R1, or the like, when the determination unit 62 determines that the condition is the partial movement condition, the endoscope 30 is not moved because the bending section 12 of the overtube 10 is not bent. Meanwhile, in the case in which the knife 26 is moved beyond the range R1, or the like, when the determination unit 62 determines that the condition is the entire movement condition, while the bending section 12 is bent, the endoscope 30 is bent such that the target area P3 is projected in the reference area G5 of the image G4.

For this reason, movement of the image displayed on the display 50 can be suppressed. In particular, since the endoscope 30 is not moved when the knife 26 is moved within the range R1, the operator O can easily recognize the image displayed on the display 50.

The endoscope 30 is bent based on the movement amount of the manipulation wire detected by the traction amount detection sensor 17. For this reason, the direction of the endoscope 30 can be easily and rapidly adjusted, for example, without calculation of the image processing for detecting the position of the target area P3 in order to adjust the direction of the endoscope 30.

The driving amount calculator 67 of the driving unit 63 has the field-of-vision fixing mode and the field-of-vision non-fixing mode in the imaging section control mode. The driving amount calculator 67 is configured such that these modes can be switched by the changeover switch 44a of the foot switch 44. As the imaging section control mode is configured as described above, switching between when only the knife 26 of the treatment tool 20 is moved without moving the image (the field-of-vision fixing mode) and when the image is moved with the knife 26 (the field-of-vision non-fixing mode) can be performed. For this reason, manipulation performance of the operator O can be improved.

Since the orientation of the knife 26 as well as the position of the knife 26 is controlled, a state of the knife 26 in the space can be more precisely controlled.

In the embodiment, the target area P3 is automatically set with respect to a portion of the large intestine P1 projected to the central part of the reference area G5 of the image when the determination unit 62 determines that the condition is the entire movement condition. However, the target area P3 of the large intestine P1 may be set as the operator O manipulates the confirmation switch 44b, or the like.

Specifically, when the operator O manipulates the confirmation switch 44b to input the confirmation instruction, the portion of the large intestine P1 projected to the center of the image may be set to the target area P3. Accordingly, the target area P3 can be easily set. As the target area P3 can be set by the operator O, the target area P3 can be specifically set in accordance with an intention of the operator O.

In the modified example, while the portion of the large intestine P1 projected to the center of the image is set to the target area P3, the portion of the image set to the target area P3 is not limited to the center but may be an edge part, a corner part, or the like.

In the embodiment, the endoscope 30 is inserted through the channel 18 of the overtube 10. However, the proximal end section of the endoscope 30 may be attached to the distal end surface 11a of the overtube 10.

A distance sensor configured to measure the distance between the target tissue P2 of the large intestine P1 and the distal end surface 11a may be provided at the distal end rigid section 11 of the overtube 10 such that the distance between the target tissue P2 of the large intestine P1 and the distal end surface 11a can be adjusted.

Second Embodiment

A second embodiment of the present invention is described with reference to FIGS. 9, 12, and 14 to 16. In the second embodiment, the same components as the first embodiment are designated by the same reference numerals, description thereof is omitted, and only different points are described.

Figure 14:
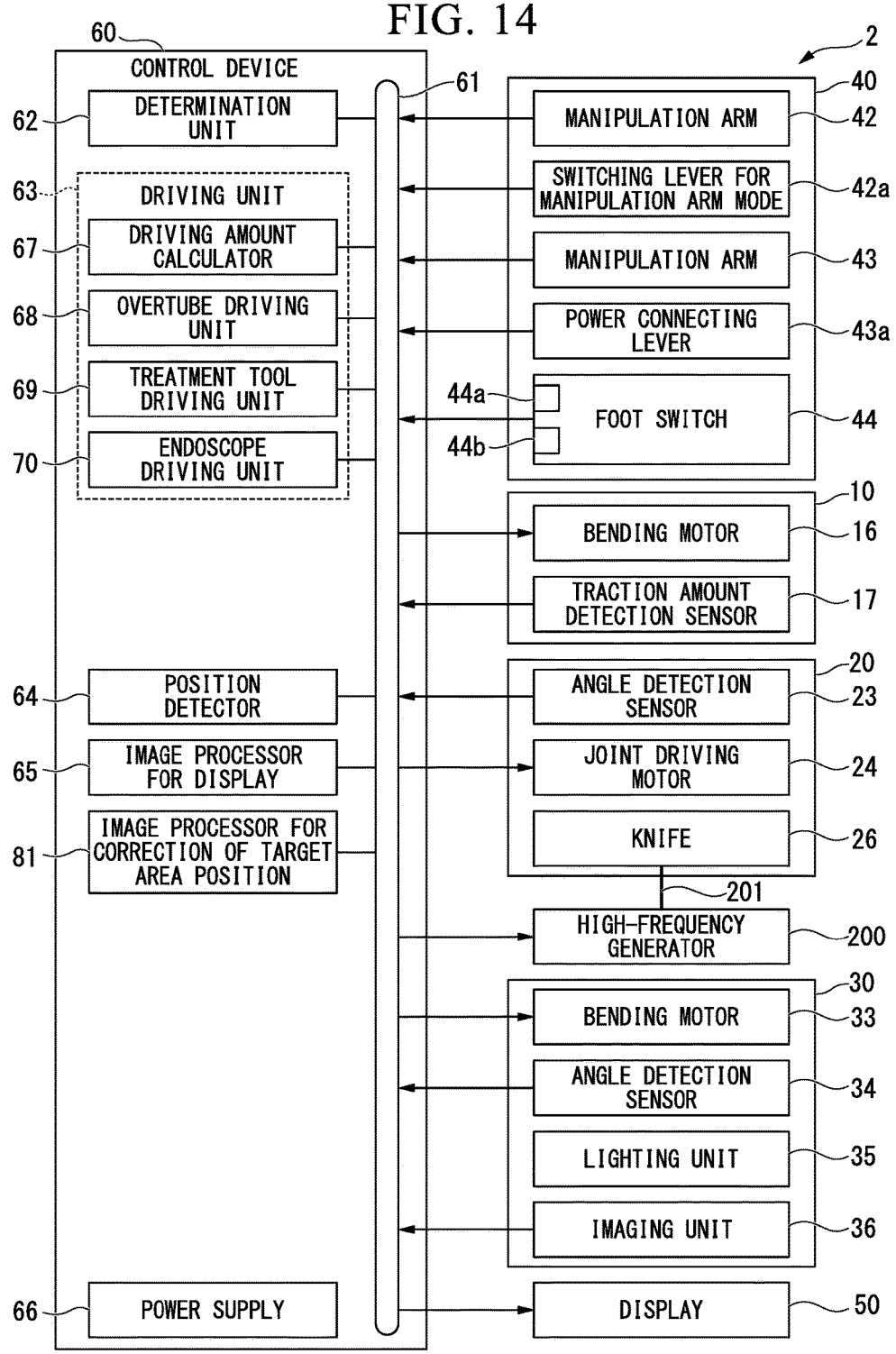
FIG. 14 is a block diagram of a medical manipulator according to a second embodiment of the present invention.

As shown in FIG. 14, a medical manipulator 2 according to the embodiment includes an image processor 81 for correction of a target area position provided at the control device 60, in addition to the components of the medical manipulator 1 according to the first embodiment.

The image processor 81 detects a position of the target area P3 in the image by performing known image processing with respect to the image acquired by the imaging unit 36. For example, the endoscope 30 is bent when the target area P3 is moved by a distance L1 to arrive at the edge part of the reference area G5 as shown in FIG. 12 from a state in which the target area P3 is disposed at the central part of the reference area G5 as shown in FIG. 8, and the target area P3 is moved to the central part of the reference area G5 as shown in FIG. 8.

In the above-mentioned first embodiment, the endoscope 30 is bent based on the movement amount of the manipulation wire detected by the traction amount detection sensor 17. On the other hand, in the embodiment, the endoscope 30 is bent based on the image acquired by the imaging unit 36.

According to the medical manipulator 2 according to the embodiment having the above-mentioned configuration, when the manipulation unit 40 is manipulated to move the treatment tool 20, movement of the image displayed on the display 50 can be suppressed and the operator O can easily recognize the image.

As the endoscope 30 is bent based on the position of the target area P3 in the image, for example, even when the manipulation wire is elongated and the relationship of the bending amount of the bending section 12 with respect to the movement amount of the manipulation wire specified in the table stored in the memory is varied, the position of the target area P3 can be compensated and the target area P3 can be more precisely moved to the central part of the reference area G5.

Even when operations of the overtube 10 and the endoscope 30 are complicated, the target area P3 can be precisely moved to the central part of the reference area G5.

Figure 15:
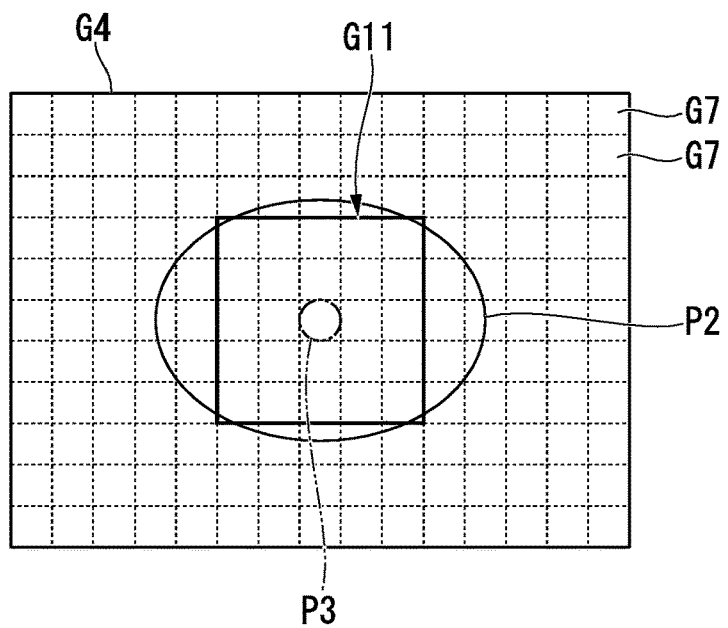
FIG. 15 is a view showing a positional relationship between a reference area and a target area of an image acquired by the medical manipulator in a modified example of the medical manipulator according to the second embodiment of the present invention.

In the embodiment, the size of the reference area G5 may be varied. That is, while the reference area G5 is constituted by nine pixels G7, a reference area G11 shown in FIG. 15 is constituted by twenty five pixels G7 configured in a rectangular shape as a whole. In the modified example, the size of the reference area G11 is set to be larger than that of the reference area G5. The reference area G11 is set to the central part of the image G4.

Figure 16:
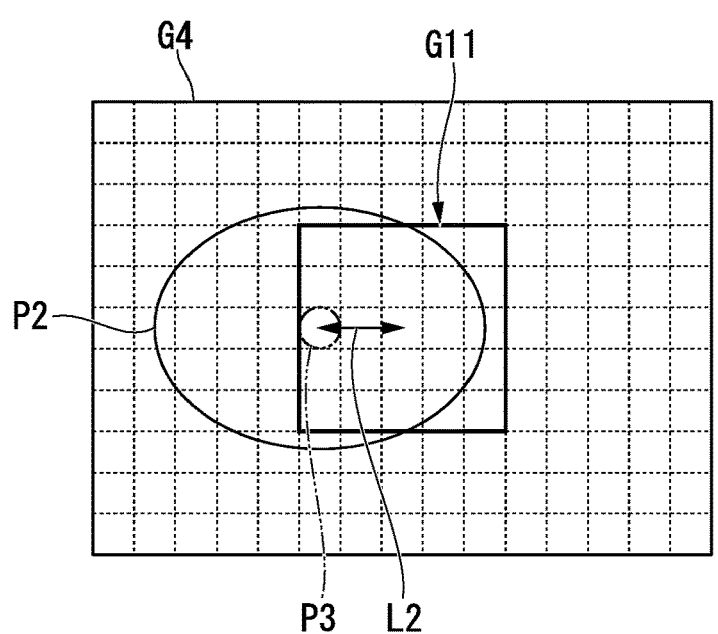
FIG. 16 is a view showing a state in which the target area is moved with respect to the reference area in the image acquired by the medical manipulator.

For example, the endoscope 30 is bent when the target area P3 is moved by a distance L2 to arrive at the edge part of the reference area G11 as shown in FIG. 16 from a state in which the target area P3 is disposed at the central part of the reference area G11 as shown in FIG. 15, and the target area P3 is moved to the central part of the reference area G11 as shown in FIG. 15. The distance L2 of this case is larger than the distance L1. That is, in the modified example, the time from starting movement of the target area P3 to starting bending of the endoscope 30 is larger than that in the above-mentioned embodiment.

According to the modified example of the medical manipulator 2 having the above-mentioned configuration, as the size of the reference area is adjusted, precision of the endoscope 30 following the movement of the target area P3 or stability of the operation of the endoscope 30 can be adjusted. That is, while the following precision is decreased as the reference area is increased, the stability of the operation is increased.

There are a portion in which the image processing is easily performed and a portion in which the image processing is not easily performed due to a shape, a color, or the like, of the tissue in the large intestine P1. The size of the reference area may be set in accordance with ease of the image processing or the like.

In the modified example, the size of the reference area G11 is set to be larger than that of the reference area G5. However, the size of the reference area G11 may be set to be smaller than that of the reference area G5. The shape of the reference area G5 is not limited to the rectangular shape but may be a circular shape.

The endoscope 30 is bent when the target area P3 is moved until arriving at the edge part of the reference area G5 from a state in which the target area P3 is disposed at the central part of the reference area G5. However, the endoscope 30 may be bent when the target area P3 is moved to the outside of the reference area G5 to be spaced a predetermined distance from the reference area G5 from a state in which the target area P3 is disposed at the central part of reference area G5.

Figure 17:
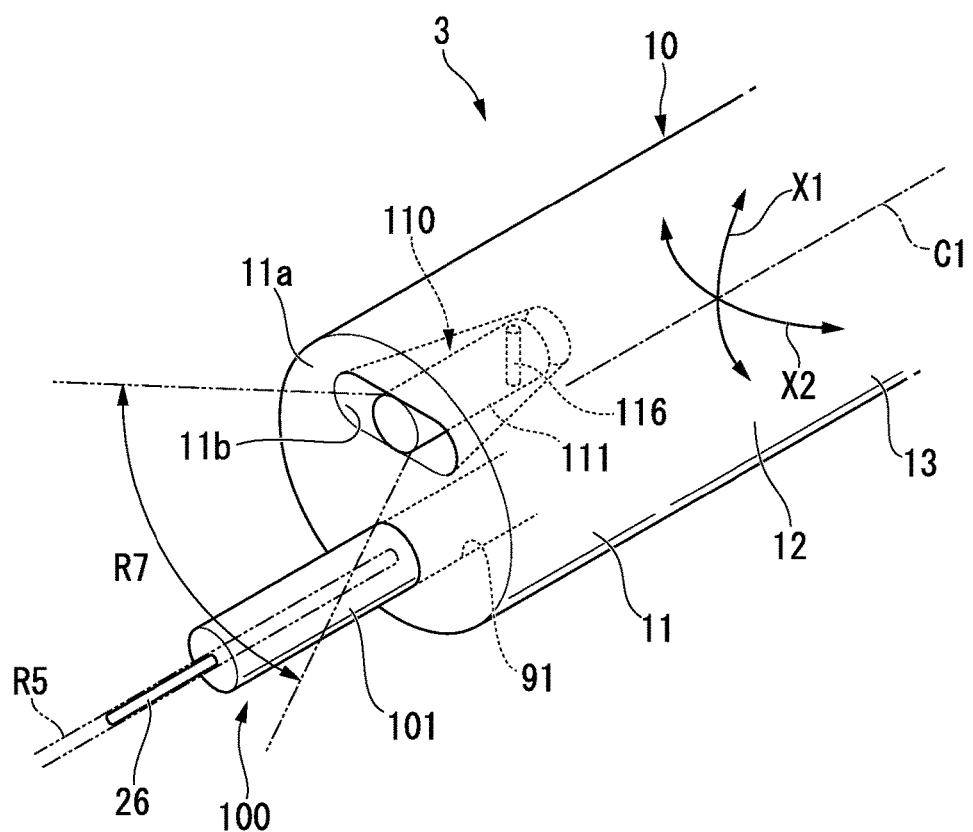
FIG. 17 is a perspective view of a distal end section of an overtube according to a modified example of the medical manipulator according to the embodiment of the present invention.

In the first embodiment and the second embodiment, a medical manipulator 3 may have a configuration as shown in FIG. 17. In the modified example, the concave section 11b is formed in the distal end surface 11a of the distal end rigid section 11. A channel 91 opened at the distal end surface 11a of the distal end rigid section 11 is formed in the overtube 10. The channel 91 is formed to extend in the direction of the axis C1.

A treatment tool 100 has a treatment tool main body 101 formed of a material having flexibility such as a silicon resin or the like in a rod shape. The treatment tool 100 has no joint like the treatment tool 20 according to the first embodiment. A proximal end section of the knife 26 formed in a rod shape is fixed to a distal end surface of the treatment tool main body 101.

The treatment tool 100 is inserted into the channel 91 of the overtube 10 so as to advance and retract. A position of the treatment tool 100 in the direction of the axis C1 with respect to the channel 91 can be manipulated by a treatment tool advance and retraction motor (an auxiliary movable section) (not shown) provided at the overtube 10. That is, as the treatment tool 100 is advanced and retracted by the treatment tool advance and retraction motor, the knife 26 can be moved in the direction of the axis C1 with respect to the distal end rigid section 11 with one degree of freedom. In the modified example, a range in which the knife 26 can be moved with respect to the distal end rigid section 11 is a range R5.

The driving amount calculator 67 determines whether the condition is the partial movement condition or the entire movement condition not by turning of the joint section 22 of the treatment tool 20 but by advancing and retracting of the treatment tool 100 in the direction of the axis C1 by the treatment tool advance and retraction motor. The driving unit 63 drives the treatment tool advance and retraction motor to advance and retract the treatment tool 100, instead of turning the joint section 22 using the joint driving motor 24 of the treatment tool 20.

An endoscope 110 has an imaging unit (not shown) provided at a distal end section of an endoscope main body 111 formed in a columnar shape. A field-of-vision range of the imaging unit is a field-of-vision range R7.

The endoscope 110 is disposed at the concave section 11b of the distal end rigid section 11. A proximal end section of the endoscope 110 is turnably supported with respect to the distal end rigid section 11 by a shaft member 116. An endoscope moving motor is connected to the endoscope 110 via a link mechanism (not shown). As the endoscope moving motor is driven, the endoscope 110 can be turned about the shaft member 116 with respect to the distal end rigid section 11.

In the modified example, the overtube 10 has two degrees of freedom of the bending section 12 and one degree of freedom by advance and retraction in the direction of the axis C1 thereof, i.e., three degrees of freedom in total. The overtube according to each embodiment of the present invention preferably has at least three degrees of freedom. The treatment tool 100 has one degree of freedom of the advance and retraction in the direction of the axis C1. The treatment tool according to each embodiment of the present invention preferably has at least one degree of freedom. The endoscope 110 has one degree of freedom around the shaft member 116. The endoscope according to each embodiment of the present invention preferably has at least one degree of freedom.

Even in the medical manipulator 3 having the above-mentioned configuration, the same effect as the medical manipulator 1 according to the first embodiment is exhibited.

In the first embodiment and the second embodiment, the orientation of the knife 26 as well as the position of the knife 26 is controlled. However, only the position of the knife 26 may be controlled.

The driving amount calculator 67 may be configured to include only the field-of-vision fixing mode, not including the field-of-vision non-fixing mode in the imaging section control mode.

The angle detection sensor 23 and the joint driving motor 24 are provided in the joint section 22 of the treatment tool 20. However, for example, the joint driving motor 24 may be provided closer to the proximal end than the treatment tool 20 in the distal end rigid section 11 or the like, and the joint section 22 may be turned by a wire (not shown) or the like connected to a driving shaft of the joint driving motor 24. The number of revolutions of the driving shaft of the joint driving motor 24 is detected by the angle detection sensor 23 such as an encoder or the like, and the angle formed by the adjacent tubular bodies 21 may be calculated from the detected number of revolutions. That is, the angle detection sensor 23 may be provided at a place other than the joint section 22.

While the treatment section is the knife 26, the kind of treatment section is not limited thereto. As the treatment section, in addition to the knife 26, a gripping section, a snare, an injection needle, or the like, may be appropriately used.

The main movable section is the bending section 12 that can be bent, and the auxiliary movable section is the joint section 22 turned around the axis C2. However, moving aspects of the main movable section and the auxiliary movable section may be appropriately selected, and the main movable section or the auxiliary movable section may be moved along the reference line in a straight shape.

Hereinabove, while preferred embodiments of the present invention have been described, the present invention is not limited to the embodiments. Additions, omissions, substitutions, and other modifications can be made to the present invention without departing from the scope of the present invention. The present invention is not limited to the above-mentioned description but is limited by only the scope of the appended claims.

What is claimed is:

1. A medical manipulator comprising:
   an insertion section configured to be inserted into a body, the insertion section comprising:
   a main movable mechanism configured to be controlled to move a distal end of the insertion section;
   a first manipulator comprising:
   a treatment device; and
   a first joint configured to be controlled to move the treatment device with respect to the distal end of the insertion section with at least one degree of freedom;
   a second manipulator comprising:
   an image sensor configured to acquire an image in a field-of-vision range; and
   a second joint configured to be controlled to move the image sensor with respect to the distal end of the insertion section;
   an input device configured to receive a user input and to output an instruction that specifies a position to which the treatment device is to be moved; and
   a controller configured to:
   determine whether a movement control to move the treatment device to the position specified in the instruction is:
   a first type of movement control in which only controlling the first joint to move the treatment device without controlling the main movable mechanism to move the distal end of the insertion section is sufficient to move the treatment device to the position specified in the instruction; or
   a second type of movement control in which both of controlling the first joint and controlling the main movable mechanism is required, to move the treatment device to the position specified in the instruction; and
   when the controller determines that the first type of movement control is sufficient, the controller is configured to control only the first joint to move the treatment device to the position specified in the instruction; and
   when the controller determines that the second type of movement control is required, the controller is configured to:
   control the first joint and the main movable mechanism to move the treatment device to the position specified in the instruction; and
   control the second joint to move the image sensor such that a target area of a test object is projected in a predetermined reference area that forms a portion of the image.

2. The medical manipulator according to claim 1, wherein a proximal end of the of the first manipulator is attached to the distal end of the insertion section, and wherein the first joint is arranged to be closer to the proximal end of the first manipulator than the treatment device.

3. The medical manipulator according to claim 1, wherein the insertion section defines a channel that has an opening at the distal end of the insertion section, and wherein the first manipulator is configured to be advanced through the channel and past the opening, and retracted past the opening and through the channel.

4. The medical manipulator according to claim 1, wherein when the controller determines that the second type of movement control is required, the controller is configured to:
   determine a movement amount of the first joint; and
   control the second joint to move the image sensor according to the movement amount of the first joint determined.

5. The medical manipulator according to claim 1,
wherein the controller is configured to set one or more of a size and a shape of the predetermined reference area.

6. The medical manipulator according to claim 1,
wherein the input device is configured to receive an instruction specifying the target area, and
wherein the controller is configured to set the target area of the test object based on the instruction specifying the target area received by the input device.

7. The medical manipulator according to claim 1,
wherein the input device is configured to receive a confirmation input and to output a confirmation instruction, and
wherein the controller is configured to set a portion of the test object projected to a center of the image as the target area in response to the confirmation instruction.

8. The medical manipulator according to claim 1,
wherein the input device is configured to receive a changeover user input and to output a changeover instruction, and
wherein when the controller determines that the second type of movement control is required, the controller is configured to:
control the first joint and the main movable mechanism to move the treatment device to the position specified in the instruction;
determine whether a changeover instruction has been output by the input device; and
when the controller determines that the changeover instruction has been output by the input device, control the second joint to move the image sensor such that the target area of the test object is projected in to the predetermined reference area that forms a portion of the image.

9. The medical manipulator according to claim 1,
wherein when the controller determines that the second type of movement control is required, the controller is configured to control the second joint to move the image sensor according to the image in the field-of-vision range.

10. The medical manipulator according to claim 1,
wherein the input device is configured to output the instruction that specifies the position to which the treatment device is to be moved and an orientation to which the treatment device is to be oriented, and
wherein when the controller determines that the second type of movement control is required, the controller is configured to:
control the first joint and the main movable mechanism to move the treatment device to the position and the orientation specified in the instruction; and
control the second joint to move the image sensor such that the target area of the test object is projected in the predetermined reference area that forms a portion of the image.

11. A method for controlling a medical manipulator, the medical manipulator comprising:
an insertion section configured to be inserted into a body, the insertion section comprising:
a main movable mechanism configured to be controlled to move a distal end of the insertion section;
a first manipulator comprising:
a treatment device; and
a first joint configured to be controlled to move the treatment device with respect to the distal end of the insertion section with at least one degree of freedom;
a second manipulator comprising:
an image sensor configured to acquire an image in a field-of-vision range; and
a second joint configured to be controlled to move the image sensor with respect to the distal end of the insertion section; and
an input device configured to receive a user input and to output an instruction that specifies a position to which the treatment device is to be moved,
wherein the method comprises:
determining, by a controller, whether a movement control to move the treatment device to the position specified in the instruction is:
a first type of movement control in which only controlling the first joint to move the treatment device without controlling the main movable mechanism to move the distal end of the insertion section is sufficient to move the treatment device to the position specified in the instruction; or
a second type of movement control in which both of controlling the first joint and controlling the main movable mechanism is required, to move the treatment device to the position specified in the instruction; and
when the first type of movement control is determined to be sufficient, controlling, by the controller, only the first joint to move the treatment device to the position specified in the instruction; and
when the second type of movement control is determined to be required:
controlling, by the controller, the first joint and the main movable mechanism to move the treatment device to the position specified in the instruction; and
controlling, by the controller, the second joint to move the image sensor such that a target area of a test object is projected in a predetermined reference area that forms a portion of the image.

12. The method according to claim 11, further comprising:
when the second type of movement control is determined to be required:
determining, by the controller, a movement amount of the first joint; and
controlling, by the controller, the second joint to move the image sensor according to the movement amount of the first joint determined.

* * * * *